US011311636B2

(12) United States Patent
Engell et al.

(10) Patent No.: US 11,311,636 B2
(45) Date of Patent: Apr. 26, 2022

(54) RADIOTRACER COMPOSITIONS AND METHODS

(71) Applicant: GE Healthcare Limited, Buckinghamshire (GB)

(72) Inventors: Torgrim Engell, Oslo (NO); Gareth Simon Getvoldsen, Amersham (GB); Andreas Richard Meijer, Oslo (NO); Imtiaz Ahmed Khan, Amersham (GB); Graeme McRobbie, Amersham (GB); Robert James Nairne, Amersham (GB)

(73) Assignee: GE HEALTHCARE LIMITED, Buckinghamshire (GB)

( * ) Notice: Subject to any disclaimer, the term of this patent is extended or adjusted under 35 U.S.C. 154(b) by 110 days.

(21) Appl. No.: 16/375,223

(22) Filed: Apr. 4, 2019

(65) Prior Publication Data

US 2019/0275182 A1    Sep. 12, 2019

Related U.S. Application Data

(62) Division of application No. 15/102,952, filed as application No. PCT/EP2014/078609 on Dec. 18, 2014, now Pat. No. 10,300,156.

(30) Foreign Application Priority Data

Dec. 18, 2013  (GB) ..................... 1322456

(51) Int. Cl.
*A61K 51/08*  (2006.01)
*C07B 59/00*  (2006.01)
*A61K 51/04*  (2006.01)

(52) U.S. Cl.
CPC ............ *A61K 51/088* (2013.01); *A61K 51/04* (2013.01); *C07B 59/008* (2013.01)

(58) Field of Classification Search
CPC ...... A61K 51/00; A61K 51/08; A61K 51/088; A61K 51/04; A61K 38/00; A61K 2121/00; A61K 2123/00; A61P 35/00; C07B 59/008
USPC .......... 424/1.11, 1.65, 1.69, 1.81, 1.85, 1.89, 424/9.1, 9.2, 9.4, 9.45, 9.453, 9.6; 514/1, 514/1.1, 19.2, 19.3, 19.4, 19.5, 19.6, 21.3; 530/300, 324
See application file for complete search history.

(56) References Cited

U.S. PATENT DOCUMENTS

| | | | |
|---|---|---|---|
| 5,961,955 A * | 10/1999 | Shochat | A61P 37/00 424/1.69 |
| 7,018,614 B2 | 3/2006 | Kiselev et al. | |
| 7,597,875 B2 | 10/2009 | Archer et al. | |
| 7,902,332 B2 | 3/2011 | De Jesus et al. | |
| 8,044,175 B2 | 10/2011 | Dransfield et al. | |
| 8,197,793 B2 | 6/2012 | Cuthbertson et al. | |
| 8,415,510 B2 * | 4/2013 | Engell | C07C 269/06 528/272 |
| 8,431,111 B2 * | 4/2013 | Nairne | A61K 49/0032 424/1.11 |
| 8,435,454 B2 | 5/2013 | Elizarov et al. | |
| 8,529,874 B2 * | 9/2013 | Johannesen | A61P 35/00 424/9.6 |
| 8,557,776 B2 | 10/2013 | Lehmann et al. | |
| 8,568,693 B2 | 10/2013 | Danikas et al. | |
| 9,000,124 B2 | 4/2015 | Dransfield et al. | |
| 9,180,213 B2 * | 11/2015 | Engell | A61K 51/082 |
| 9,259,496 B2 * | 2/2016 | Iveson | A61K 51/08 |
| 9,493,504 B2 * | 11/2016 | Indrevoll | A61K 51/088 |
| 9,533,059 B2 * | 1/2017 | Iveson | A61K 51/088 |
| 9,956,303 B2 * | 5/2018 | Dalsgaard | G01N 33/5017 |
| 9,987,382 B2 * | 6/2018 | Engell | A61K 51/082 |
| 10,300,156 B2 * | 5/2019 | Engell | A61K 51/04 |
| 2009/0274623 A1 | 11/2009 | Smith et al. | |
| 2010/0068150 A1 | 3/2010 | Bogyo et al. | |
| 2013/0149241 A1 | 6/2013 | Iveson et al. | |
| 2013/0209358 A1 | 8/2013 | Barnett et al. | |
| 2014/0004041 A1 | 1/2014 | Iveson et al. | |
| 2014/0335022 A1 | 11/2014 | Dalsgaard et al. | |
| 2016/0166717 A1 | 6/2016 | Skjold et al. | |
| 2016/0303262 A1 | 10/2016 | Engell et al. | |

FOREIGN PATENT DOCUMENTS

| | | |
|---|---|---|
| CL | 00339 A | 12/1994 |
| CN | 103153350 A | 6/2013 |
| EP | 1952826 A1 | 8/2008 |
| EP | 2287197 A1 | 2/2011 |
| EP | 3036208 A1 | 6/2016 |
| EP | 2605802 B1 | 4/2017 |
| JP | 2006505610 A | 2/2006 |
| JP | 2009542689 A | 12/2009 |
| JP | 2010520229 A | 6/2010 |
| JP | 2010526859 A | 8/2010 |

(Continued)

OTHER PUBLICATIONS

Wickstrom et al., Journal of Nuclear Medicine, May 2012, vol. 53, No. Supplement 1, p. 1461. (Year: 2012).*
China First Office Action corresponding to Chinese Application No. 201480069324.9, dated Nov. 9, 2018 (18 pages).
China First Search Report corresponding to Chinese Application No. 201480069324.9, dated Oct. 17, 2018.
Japanese Office Action corresponding to JP Application No. 2016-539089, dated Sep. 4, 2018.
China First Search Report corresponding to Chinese Application No. 201480046209.X, dated Aug. 20, 2014.
China First Office Action corresponding to Chinese Application No. 201480046209.X, dated Dec. 5, 2016 (11 pages).

(Continued)

*Primary Examiner* — D. L. Jones
(74) *Attorney, Agent, or Firm* — Jeff B. Vockrodt; Culhane Meadows, PLLC

(57) ABSTRACT

The present invention relates to the field of radiopharmaceuticals for in vivo imaging, in particular to radiotracer compositions which comprises $^{18}$F-labelled c-Met binding peptides. The invention provides said compositions, as well as associated automated methods of preparation and cassettes.

8 Claims, 2 Drawing Sheets

(56) References Cited

FOREIGN PATENT DOCUMENTS

| | | |
|---|---|---|
| JP | 2011513211 A | 4/2011 |
| JP | 5309141 B2 | 10/2013 |
| JP | 5341757 B2 | 11/2013 |
| JP | 2013540702 A | 11/2013 |
| JP | 6014592 B2 | 10/2016 |
| WO | 02070018 A2 | 9/2002 |
| WO | 03006070 A2 | 1/2003 |
| WO | 03011115 A2 | 2/2003 |
| WO | 03057155 A2 | 7/2003 |
| WO | 2004062568 A2 | 7/2004 |
| WO | 2004078778 A2 | 9/2004 |
| WO | 2004080492 A1 | 9/2004 |
| WO | 2006030291 A2 | 3/2006 |
| WO | 2008072976 A2 | 6/2008 |
| WO | 2008139207 A2 | 11/2008 |
| WO | 2009016180 A2 | 2/2009 |
| WO | 2009016181 A2 | 2/2009 |
| WO | 2009027706 A2 | 3/2009 |
| WO | 2009106566 A2 | 3/2009 |
| WO | 2011008990 A1 | 1/2011 |
| WO | 2011048029 A1 | 4/2011 |
| WO | 2012022676 A1 | 2/2012 |
| WO | WO-2012022676 A1 * 2/2012 ............. A61K 49/00 | |
| WO | 2012072728 A1 | 6/2012 |
| WO | 2012072736 A2 | 6/2012 |
| WO | 2012076697 A1 | 6/2012 |
| WO | 2012087725 A1 | 6/2012 |
| WO | 2013092742 A1 | 6/2013 |
| WO | 2013174909 A1 | 11/2013 |
| WO | 2015024983 A1 | 2/2015 |
| WO | 2012087912 A1 | 6/2016 |

OTHER PUBLICATIONS

International Search Report and Written Opinion corresponding to International Application No. PCT/EP2014/067775, dated Dec. 17, 2014 (7 pages).
Great Britain Search Report corresponding the GB Application No. 1314936.4, dated Feb. 14, 2014 (3 pages).
International Search Report and Written Opinion corresponding to International Application No. PCT/EP2014/078608, dated Mar. 5, 2015 (8 page).
China Office Action corresponding Chinese Application No. 201480046209.X, dated Aug. 18, 2017 (28 pages).
Poethko et al., "Two-Step Methodology for High-Yield Routine Radiohalgenation of Peptides: 18F-Labeled RGD and Octreotide Analogs", Journal of Nuclear Medicine, vol. 45, No. 5, May 2003, pp. 892-902.
Kilbourn et al., "Fluorine-18 Labeling of Proteins", J Nucl Med, 1987, pp. 462-470.
International Search Report and Written Opinion corresponding to International Application No. PCT/EP2011/063890, dated Dec. 19, 2011 (14 pages).
Great Britain Search Report corresponding to GB Application No. 1013808.9, dated Dec. 15, 2010.
Flavell et al. "Site-Specific 18F-Labeling of the Protein Hormone Leptin Using a General Two-Step Ligation Procedure", Journal of the American Chemical Society, 2008, vol. 1330, pp. 9106-9112.
Great Britain Search Report corresponding to GB Application No. 1103696.9, dated Aug. 10, 2011.
International Search Report and Written Opinion corresponding to International Application No. PCT/EP2012/053614, dated May 16, 2012 (10 pages).
Japan Office Action corresponding Japanese Patent Application No. 2014-547982, dated Jan. 17, 2017 (4 pages).
International Preliminary Report on Patentability corresponding to PCT Patent Application No. PCT/EP2012/076196, dated Jun. 24, 2014 (8 pages).
Garcia, et al., "C-Met Overexpression in Inflammatory Breast Carcinomas: Automated Quantification on Tissue Microarrays", British Journal of Cancer, vol. 96, 2007, pp. 329-335.
Great Britain Search Report corresponding to GB Application No. 1121914.4, dated Apr. 30, 2012.
International Search Report and Written Opinion corresponding to International Application No. PCT/EP2012/076196, dated Mar. 28, 2013.
Japanese Office Action corresponding to JP Application No. 2013-524419, dated May 17, 2016.
International Search Report and Written Opinion corresponding to International Application No. PCT/EP2014/078609, dated Apr. 7, 2015 (15 pages).
Great Britain Search Report corresponding to GB Application No. 1322456.3, dated Aug. 18, 2014 (3 pages).
Chile Office Action corresponding to Chilean Application No. 483-2013, dated Feb. 18, 2013.

* cited by examiner

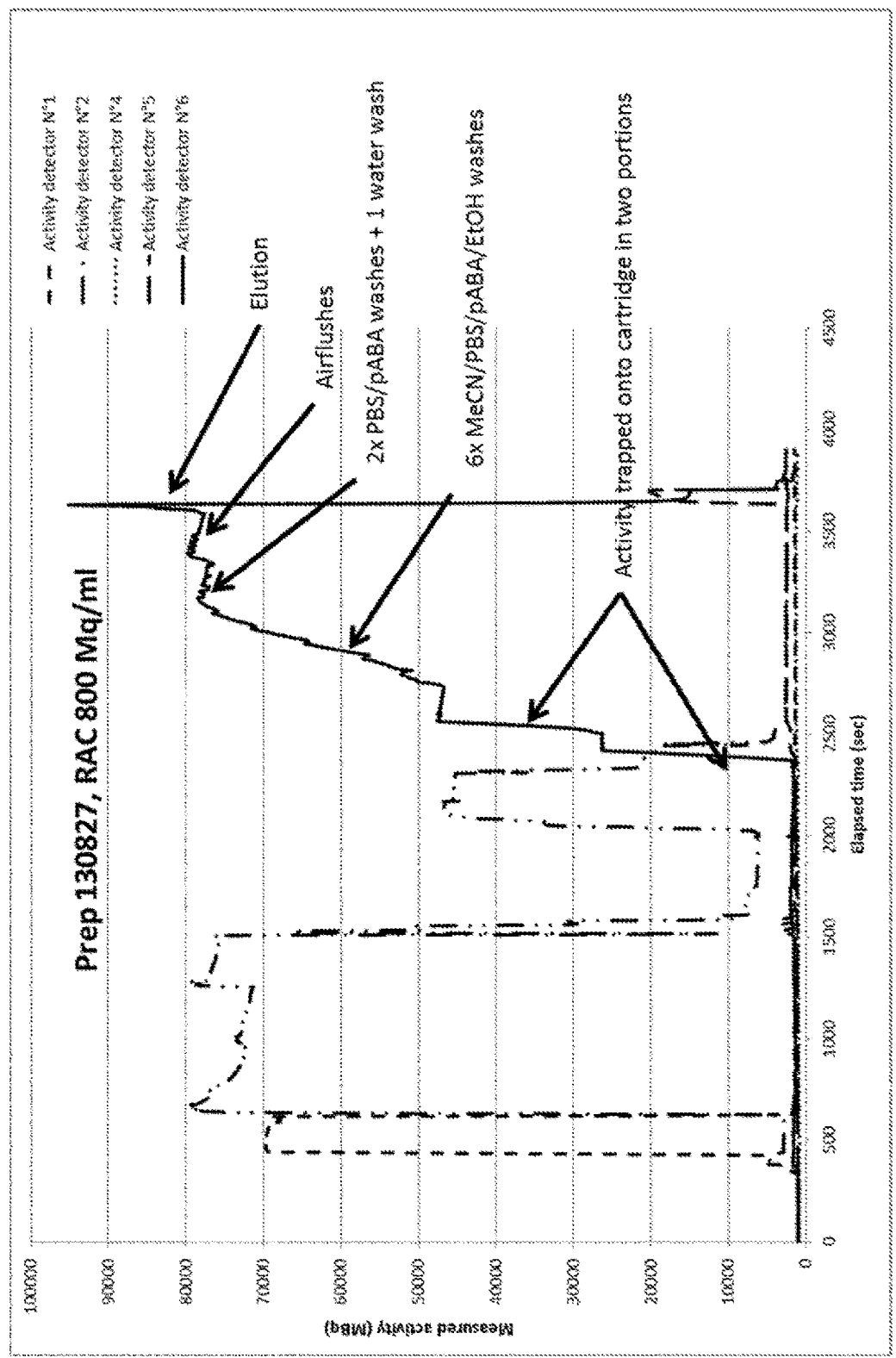
Figure 1: Radioactive Elution Profile During SPE.

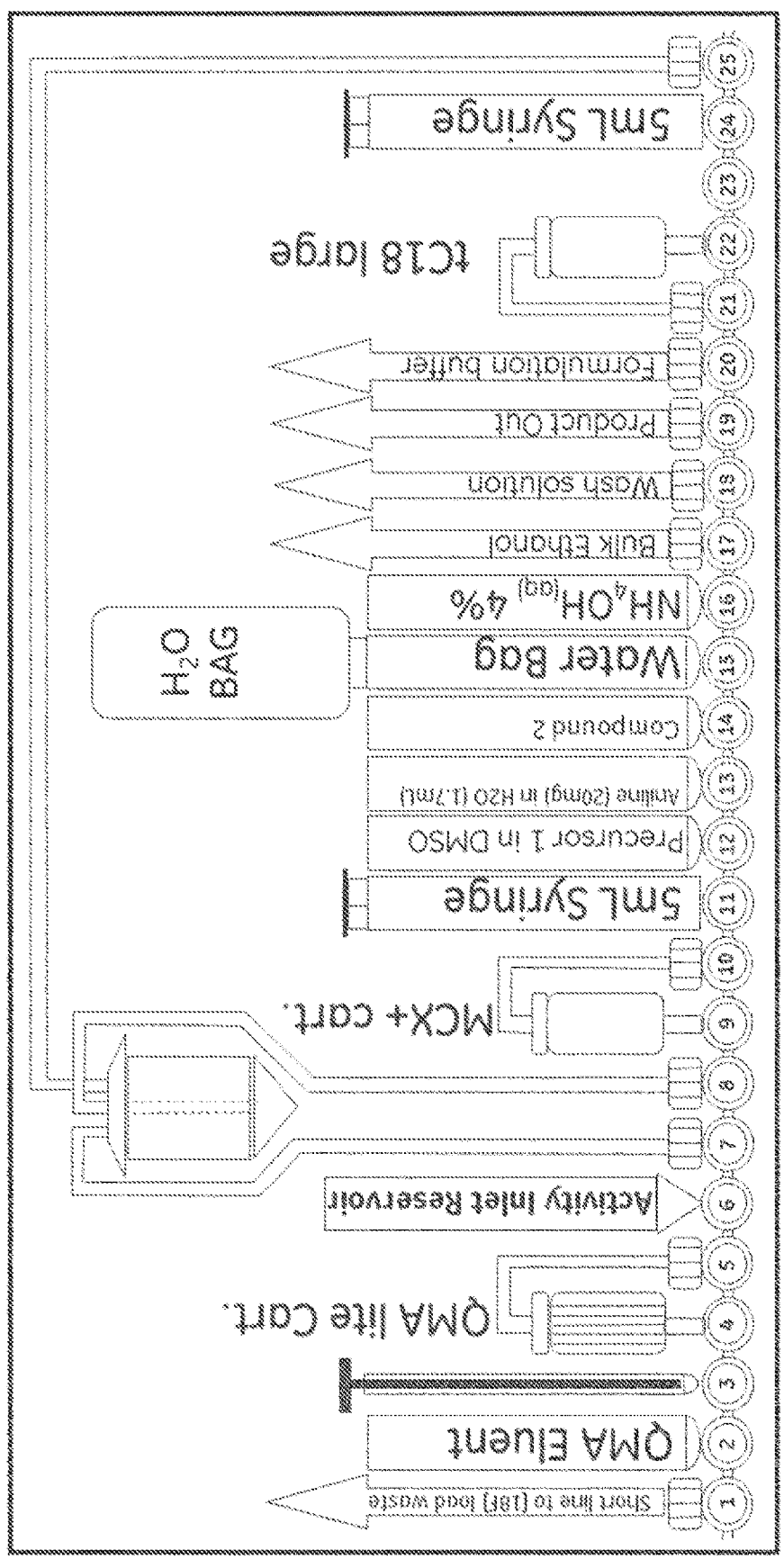
Figure 2: Casette Configuration.

RADIOTRACER COMPOSITIONS AND METHODS

CROSS-REFERENCE TO RELATED APPLICATIONS

This application is a divisional of U.S. patent application Ser. No. 15/102,952, filed on Jun. 9, 2016, which is a filing under 35 U.S.C. 371 of international application number PCT/EP2014/078609, filed Dec. 18, 2014, which claims priority to GB application number 1322456.3, filed Dec. 18, 2013, the entire disclosures of each of which are hereby incorporated by reference.

FIELD OF THE INVENTION

The present invention relates to the field of radiopharmaceuticals for in vivo imaging, in particular to radiotracer compositions which comprises $^{18}$F-labelled c-Met binding peptides. The invention provides said compositions, as well as associated automated methods of preparation and cassettes.

BACKGROUND TO THE INVENTION

Hepatocyte growth factor (HGF), also known as scatter factor (SF), is a growth factor which is involved in various physiological processes, such as wound healing and angiogenesis. The high affinity interaction of HGF interaction with its receptor (c-Met) is implicated in tumour growth, invasion and metastasis.

c-Met has been shown to be involved in tumour growth, invasion and metastasis in many human cancers of epithelial origin. c-Met is expressed by most carcinomas and its elevated expression relative to normal tissue has been detected in cancers of: lung, breast, colorectal, pancreatic, head and neck, gastric, hepatocellular, ovarian, renal, glioma, melanoma and a number of sarcomas. In colorectal carcinoma (CRC), over-expression of c-Met has been detected in dysplastic aberrant crypt foci, the earliest pre-neoplastic lesions of the disease. In head and neck squamous cell cancer, c-Met is reportedly expressed or overexpressed in roughly 80% of primary tumours. In prostate cancer metastasis to bone, c-Met was reported overexpressed in over 80% of bone metastasis.

Under normal conditions, c-Met is expressed on epithelial cells and activated in a paracrine fashion, by mesenchymally derived HGF. The activation of c-Met in normal cells is a transient event and is tightly regulated. In tumour cells, however, c-Met can be constitutively active. In cancer, aberrant c-Met stimulation can be achieved through c-Met amplification/over-expression, activating c-Met mutations (e.g. structural alterations) and acquisition of autonomous growth control through creation of autocrine signalling loops. In addition, a defective down-regulation of the c-Met receptor will also contribute to aberrant c-Met expression in the cell membrane. While the over-expression of c-Met is HGF dependent (autocrine/paracrine), structural alterations caused by mutations are HGF independent (e.g. loss of extracellular domain).

Poethko et al [J. Nucl. Med., 45(5), 892-902 (2004)] disclose a method of radiolabelling peptides with the radioisotope $^{18}$F, wherein an aminoxy-functionalised peptide is condensed with [$^{18}$F]-fluorobenzaldehyde to give a labelled peptide having an oxime ether linkage as follows:

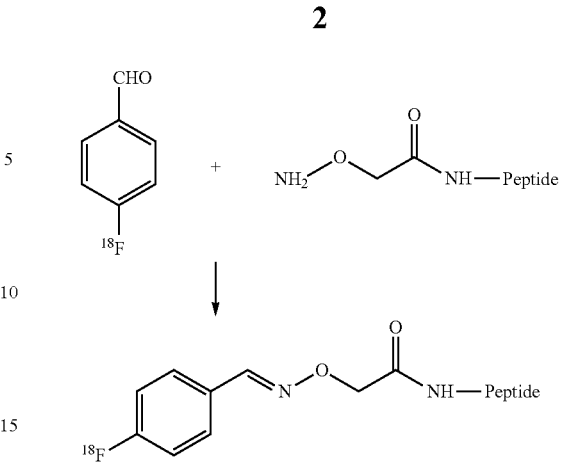

Schottelius et al [Bioconj. Chem., 19(6), 1256-1268 (2008)] further developed the method of Poethko et al. Schottelius et al use an aminoxy-functionalised peptide wherein the amine of the aminoxy group is protected with an N-Boc (Boc=tert-butyloxycarbonyl) protecting group. The desired aminoxy-functionalised peptide is generated in situ in the presence of [$^{18}$F]-fluorobenzaldehyde via deprotection of the N-Boc group at acidic pH (pH=2) at 75° C. Schottelius et al used a 5-fold molar excess of the Boc-protected precursor, because the deprotection was not quantitative under the reaction conditions.

Mezo et al [J. Pept. Sci., 17, 39-46 (2010)] describe some of the problems associated with the above oxime ligation chemistry of Boc-protected aminoxy-functionalised peptides. Thus, it is known that the Boc-aminoxy reagent can acylate formed Boc-protected aminoxy-peptide, leading to undesirable by-products. It is also known that the reactivity of the free aminoxy group of the functionalised peptide is high towards carbonyl compounds. Consequently, unwanted condensation can occur with any adventitious aldehydes or ketones present either in the reaction mixture or in any subsequent purification steps. Such aldehydes or ketones could be traces of acetone present in the solvents used, or formaldehyde (e.g. from plasticizers). Mezo et al are interested in solving this problem for both the conjugation of anti-cancer drugs and of [$^{18}$F]-fluorobenzaldehyde to peptides. Mezo et al solve the problem by carrying out the deprotection of the Boc-aminoxy peptide in the presence of a tenfold molar excess of free (aminoxy)acetic acid (Aoa) as a 'carbonyl capture agent'. The deprotected aminoxy-peptide and excess Aoa is then lyophilised and stored at 4° C. Immediately prior to the oxime ligation reaction, the lyophilised mixture is reconstituted, and excess Aoa is separated by HPLC or Sep-Pak plus C18 cartridge. Mezo et al provide an example in which non-radioactive (i.e. $^{19}$F) 4-fluorobenzaldehyde is conjugated to an aminoxy-functionalised somatostatin peptide using this technique. Mezo et al do not provide any data on $^{18}$F-radiolabelling.

WO 2012/022676 discloses an imaging agent which comprises an $^{18}$F-radiolabelled 18 to 30-mer c-Met binding cyclic peptide (cMBP) of Formula I:

$$Z^1\text{-[cMBP]-}Z^2 \quad (I)$$

where:
cMBP is of Formula II:

where Q is the amino acid sequence (SEQ-1):
-Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$- wherein $X^1$ is Asn, His or Tyr;
$X^2$ is Gly, Ser, Thr or Asn;
$X^3$ is Thr or Arg;
$X^4$ is Ala, Asp, Glu, Gly or Ser;
$X^5$ is Ser or Thr;

$X^6$ is Asp or Glu;
and $Cys^{a-d}$ are each cysteine residues such that residues a and b as well as c and d are cyclised to form two separate disulfide bonds;
A and A' are independently any amino acid other than Cys, with the proviso that at least one of A and A' is present and is Lys;
x and y are independently integers of value 0 to 13, and are chosen such that [x+y]=1 to 13;
$Z^1$ is attached to the N-terminus of cMBP, and is H or $M^{IG}$;
$Z^2$ is attached to the C-terminus of cMBP and is OH, $OB^c$, or $M^{IG}$,
where $B^c$ is a biocompatible cation;
each $M^{IG}$ is independently a metabolism inhibiting group which is a biocompatible group which inhibits or suppresses in vivo metabolism of the cMBP peptide;
wherein cMBP is labelled at the Lys residue of the A or A' groups with $^{18}F$.

WO 2012/022676 also discloses that the imaging agents may be used as pharmaceutical compositions, wherein said compositions preferably comprises one or more radioprotectants preferably chosen from: ethanol; ascorbic acid; para-aminobenzoic acid (i.e. 4-aminobenzoic acid or pABA); gentisic acid (i.e. 2,5-dihydroxybenzoic acid), and salts of such acids with a biocompatible cation.

WO 2012/072736 discloses the use of alternative protecting group chemistry for the aminoxy groups of functionalised biomolecules. The protected aminoxy group is of formula:

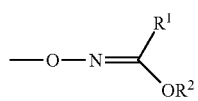

wherein:
$R^1$ and $R^2$ are independently chosen from $C_{1-3}$ alkyl, $C_{1-3}$ fluoroalkyl or $C_{4-6}$ aryl.

US 2013/0209358 A1 discloses that $^{18}F$-fluciclatide can undergo radiolysis at high radioactive concentration:

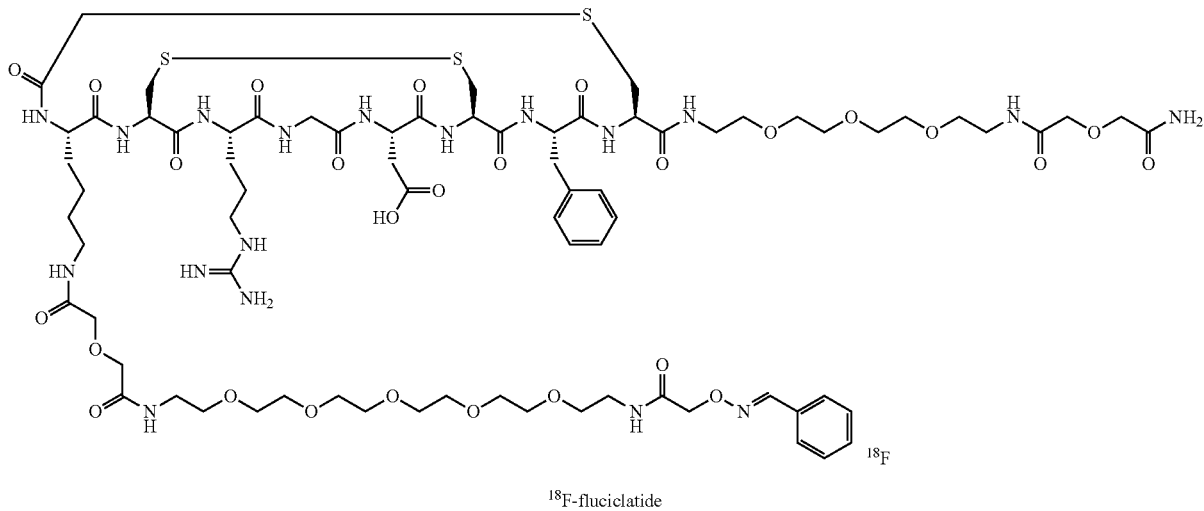

$^{18}F$-fluciclatide

US 2013/0209358 A1 reports that $^{18}F$-fluciclatide is not stabilised by ethanol, and that ascorbic acid is not ideal for automated radiosyntheses, but that 4-aminobenzoic acid (or salt thereof) is effective. US 2013/0209358 A1 teaches that the $^{18}F$-fluciclatide is first prepared, and then the radioprotectant is added.

There is therefore still a need for improved methods of preparing and purifying $^{18}F$-labelled c-Met peptide radiotracers, to give high purity compositions suitable for radiopharmaceutical applications in vivo.

The Present Invention.

The present inventors have identified and analysed the radiochemical impurities present in $^{18}F$-labelled c-Met targeting peptides, and how the levels of such impurities vary over time. That investigation led to the understanding that in-process radiolysis during attempted purification was the root cause of the RCP (radiochemical purity) problems.

This can be understood as follows. Thus, the radiotracers of the present invention, when purified and formulated for in vivo use, are present at a radioactive concentration (RAC) of approximately 500 to 700 MBq/mL (0.5 to 0.7 GBq/mL). The radiotracer may exhibit satisfactory stability, or minimal degradation under such RAC conditions. That is, however, obtained from a crude reaction mixture, where the RAC is in the range of ca. 10 to 15 GBq/mL. Furthermore, the present inventors have established that, during purification (i.e. at the end of the radiosynthesis), approximately 45 GBq of radioactivity is concentrated in a tight band on the chromatography column in a volume of less than 1 mL. That leads to an in-process RAC during purification of >45 GBq/mL. Since the purification can take 10-15 minutes, the risk of in-process radiolysis is high.

The present invention provides methods for stabilising the radiotracers whilst carrying out purification, and hence also provides improved radioactive yields and compositions. The present invention provides a method of purification of a radiotracer which comprises an $^{18}F$-labelled c-Met targeting peptide. It is in fact both a method of purification and a method of radiostabilisation (i.e. stabilising against radioactive degradation). Thus, by preventing in-process radiodegradation during purification, the present invention also improves the radiochemical purity, since impurities which might otherwise be generated are suppressed. The method also provides an improved radiochemical yield, since in-process losses during chromatography are minimised.

DETAILED DESCRIPTION OF THE INVENTION

In a first aspect, the present invention provides a radiopharmaceutical composition which comprises:
 (i) a radiotracer which comprises a c-Met binding peptide of Formula I labelled with $^{18}$F:

$$Z^1\text{-[cMBP]-}Z^2 \tag{I}$$

(ii) a radioprotectant which comprises 4-aminobenzoic acid, or a salt thereof with a biocompatible cation;
 (iii) a biocompatible carrier which comprises aqueous ethanol having an ethanol content of 0.1 to 10% v/v;
in a form suitable for mammalian administration;
where:
cMBP is the c-Met binding peptide having the amino acid sequence:
Ala-Gly-Ser-Cys$^a$-Tyr-Cys$^c$-Ser-Gly-Pro-Pro-Arg-Phe-Glu-Cys$^d$-Trp-Cys$^b$-Tyr-Glu-Thr-Glu-Gly-Thr-Gly-Gly-Gly-Lys
  wherein Cys$^{a-d}$ are each cysteine residues such that residues a and b as well as c and d are cyclised to form two separate disulfide bonds;
$Z^1$ is attached to the N-terminus of cMBP, and is $M^{IG}$;
$Z^2$ is attached to the C-terminus of cMBP and is $M^{IG}$,
$M^{IG}$ is independently a metabolism inhibiting group which is a biocompatible group which inhibits or suppresses in vivo metabolism of the cMBP peptide;
the Lys residue of the cMBP is labelled with $^{18}$F.

The term "radiotracer" has its' conventional meaning and refers to a radiopharmaceutical used to trace a physiological or biological process without affecting it. The term "radiopharmaceutical" has its' conventional meaning and refers to a radiolabelled compound administered to the mammalian body in vivo for the purpose of imaging or therapy. During chromatographic purification, such as when loaded and hence concentrated into a small volume at the top of an SPE column, the radiotracer may transiently be exposed to very high radioactive concentration ("RAC"). Thus, radiotracers which otherwise appear radiostable, may exhibit instability with consequent loss of radiochemical purity ("RCP") and/or radiochemical yield during attempted purification.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention is suitably chosen from para-aminobenzoic acid (i.e. 4-aminobenzoic acid) and salts thereof with a biocompatible cation. By the term "biocompatible cation" is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred bio compatible cations are sodium and potassium, most preferably sodium.

The "biocompatible carrier" is a fluid, especially a liquid, in which the radioconjugate can be suspended or preferably dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free water for injection, isotonic saline or phosphate buffer.

By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

By the term "peptide" is meant a compound comprising two or more amino acids, as defined below, linked by a peptide bond (ie. an amide bond linking the amine of one amino acid to the carboxyl of another).

By the term "amino acid" is meant an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure.

By the term "metabolism inhibiting group" ($M^{IG}$) is meant a biocompatible group which inhibits or suppresses enzyme, especially peptidase (e.g. carboxypeptidase), metabolism of the cMBP at either the amino terminus or carboxy terminus. Such groups are particularly important for in vivo applications since otherwise rapid metabolism would be expected with consequent loss of selective binding affinity, and are well known to those skilled in the art and are suitably chosen from, for the peptide amine terminus: N-acylated groups —NH(C=O)R$^G$ where the acyl group —(C=O)R$^G$ has R$^G$ chosen from: $C_{1-6}$ alkyl, $C_{3-10}$ aryl groups or comprises a polyethyleneglycol (PEG) building block. Preferred such amino terminus $M^{IG}$ groups are acetyl, benzyloxycarbonyl or trifluoroacetyl, most preferably acetyl.

Suitable metabolism inhibiting groups for the peptide carboxyl terminus include: carboxamide, tert-butyl ester, benzyl ester, cyclohexyl ester, amino alcohol or a polyethyleneglycol (PEG) building block. A suitable $M^{IG}$ group for the carboxy terminal amino acid residue of the cMBP is where the terminal amine of the amino acid residue is N-alkylated with a $C_{1-4}$ alkyl group, preferably a methyl group. Preferred such $M^{IG}$ groups are carboxamide or PEG, most preferred such groups are carboxamide.

The radiotracer and biocompatible carrier are supplied in a suitable vial or vessel which comprises a sealed container which permits maintenance of sterile integrity and/or radioactive safety, plus optionally an inert headspace gas (e.g. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour.

Preferred multiple dose containers comprise a single bulk vial which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use.

The radiopharmaceutical composition may contain additional optional excipients such as: an antimicrobial preservative, pH-adjusting agent, filler, solubiliser or osmolality adjusting agent. By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

By the term "solubiliser" is meant an additive present in the composition which increases the solubility of the agent of interest in the solvent. A preferred such solvent is aqueous media, and hence the solubiliser preferably improves solubility in water. Suitable such solubilisers include: $C_{1-4}$ alcohols; glycerine; polyethylene glycol (PEG); propylene glycol; polyoxyethylene sorbitan monooleate; sorbitan monooloeate; polysorbates; poly(oxyethylene)poly(oxypropylene)poly(oxyethylene) block copolymers (Pluronics™); cyclodextrins (e.g. alpha, beta or gamma cyclodextrin, hydroxypropyl-β-cyclodextrin or hydroxypropyl-γ-cyclodextrin) and lecithin.

By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such micro-organism in the pharmaceutical composition. The antimicrobial preservative may, however, also optionally be used to inhibit the growth of potentially harmful micro-organisms in one or more components of kits used to prepare said composition prior to administration. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the composition is within acceptable limits (approximately pH 4.0 to 10.5) for human or mammalian administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the composition is employed in kit form, the pH adjusting agent may optionally be provided in a separate vial or container, so that the user of the kit can adjust the pH as part of a multi-step procedure.

Preferred Features.

In the radiopharmaceutical composition of the first aspect, $Z^1$ is preferably acetyl and $Z^2$ is preferably a primary amide.

The $^{18}F$ is preferably attached to the cMBP via an oxime linkage, more preferably to an aminoxy-functionalised cMBP. The term "aminoxy-functionalised" means that the cMBP is functionalised with, or has conjugated thereto, an aminoxy group. The term "aminoxy group" has its conventional meaning, and refers to a substituent of formula —O—NH$_2$, preferably —CH$_2$—O—NH$_2$. The radiotracer of the first aspect is preferably of Formula II:

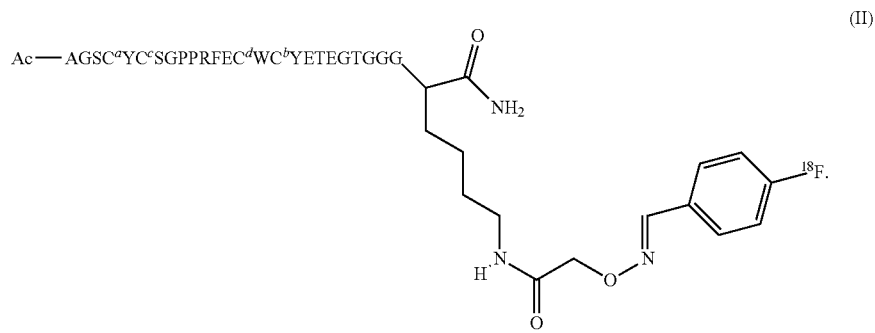

where conventional single letter amino acid abbreviations are used.

The 4-aminobenzoic acid concentration in the composition of the first aspect is preferably 1.5 to 2.5 mg/mL, more preferably 1.8 to 2.2 mg/mL, most preferably about 2.0 mg/mL.

The ethanol concentration in the composition of the first aspect is preferably 6.5 to 8.5% v/v.

The aqueous component of the biocompatible carrier in the composition of the first aspect is preferably a buffer solution of pH 6-8, more preferably a phosphate buffer.

In the radiopharmaceutical composition of the first aspect, preferably at least 90% of the $^{18}F$ radioactive content is the radiotracer of Formula (I), and less than 10% of said content is the total of [$^{18}F$]-4-fluorobenzaldehyde and [$^{18}F$]-4-fluorobenzonitrile. More preferably, at least 92% of the $^{18}F$ radioactive content is the radiotracer of Formula (I), and less than 5% of said content is the total of [$^{18}F$]-4-fluorobenzaldehyde and [$^{18}F$]-4-fluorobenzonitrile. Fluorobenzonitrile is the compound F-Ph-CN, where Ph is 1,4-phenylene. These radioactive impurities arise from previously unrecognised in-process radiolysis of the $^{18}$F-labelled cMBP of the invention, and their control gives improved radiopharmaceutical compositions.

The radiopharmaceutical compositions of the first aspect can be prepared as described in the second aspect (below).

In a second aspect, the present invention provides a method of preparation of the radiopharmaceutical composition of the first aspect, which comprises:
(A) provision of a single use cassette which comprises:
 (i) a first non-radioactive precursor, capable of reacting with [$^{18}$F]-fluoride to give [$^{18}$F]-fluorobenzaldehyde;
 (ii) a second non-radioactive precursor of Formula III, capable of reacting with [$^{18}$F]-fluorobenzaldehyde to give the radiotracer of Formula II as defined in the first aspect:

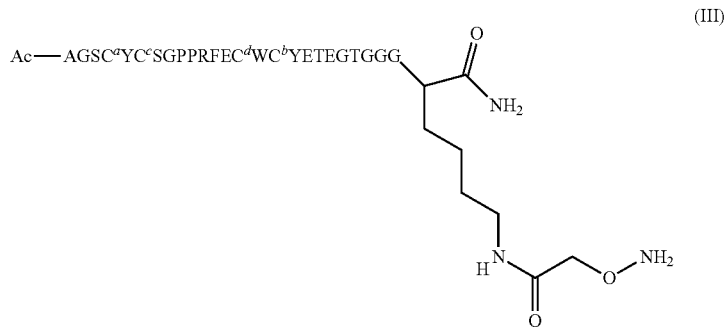

(III)

(iii) a reverse phase solid phase extraction column;
(iv) a supply of the radioprotectant as defined in the first aspect;
(v) a reaction vessel;
(vi) suitable solvents;
(B) reaction of the first precursor with [$^{18}$F]-fluoride to give [$^{18}$F]-fluorobenzaldehyde;
(C) reaction of the [$^{18}$F]-fluorobenzaldehyde from step (B) with the second precursor to give the radiotracer of Formula II;
(D) addition of said radioprotectant to the radiotracer of Formula II from step (C) to give a radiotracer solution;
(E) purification of the radiotracer solution from step (D) using said reverse phase solid phase extraction column;
(F) optionally diluting the purified [$^{18}$F]-radiotracer from step (E) with a biocompatible carrier;
(G) aseptic filtration of the optionally diluted solution from step (F) to give said radiopharmaceutical composition; wherein said cassette fits removably and interchangeably onto an automated synthesizer apparatus and said automated synthesizer apparatus is used to carry out at least steps (B)-(E).

Preferred embodiments of the radiotracer and radioprotectant in the second aspect are as described in the first aspect (above).

The term "reverse phase" refers to "reverse phase chromatographic purification", which has its conventional meaning, and refers to chromatography where the stationary phase is lipophilic and the mobile phase is hydrophilic, typically involving aqueous media. The chromatographic technique of the present invention is solid phase extraction (SPE) using either an SPE column, sometimes called an 'SPE cartridge'. Such SPE columns have the advantage that they are single use, i.e. disposable, so there is no risk of cross-contamination with other radiotracers. The reverse phase SPE cartridge of the second aspect preferably has a carbon load of 2.7 to 17%, and and is more preferably a C18 SPE cartridge, most preferably a tC18 SPE cartridge. Reverse phase SPE cartridges suitable for use in the present invention can be obtained from Waters Limited (730-740 Centennial Court, Centennial Park, Elstree, Hertfordshire, UK).

In order to obtain radiopharmaceutical compositions, the method of the second aspect is carried out using aseptic manufacture techniques in which the steps are carried out using an automated synthesizer apparatus. By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical composition is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a cassette.

By the term "cassette" is meant a unit piece of apparatus designed such that the whole unit fits removably and interchangeably onto an automated synthesizer apparatus (as defined above), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (e.g. solid phase extraction or SPE). The cassette always comprises a reaction vessel. Such reaction vessels are preferably 1 to 10 cm$^3$, most preferably 2 to 5 cm$^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture and are therefore manufactured from materials which are of pharmaceutical grade and ideally also are resistant to radiolysis.

Suitable automated synthesizers of the present invention comprise a disposable or single use cassette which comprises all the reagents, reaction vessels and apparatus necessary to carry out the preparation of a given batch of radio fluorinated radiopharmaceutical. The cassette means that the automated synthesizer has the flexibility to be capable of making a variety of different radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

In the method of the second aspect, the automated synthesizer apparatus is preferably used to carry out steps (B)-(G).

The "first non-radioactive precursor" is designed to react with [$^{18}$F]-fluoride to give [$^{18}$F]-fluorobenzaldehyde in a single step. Suitable such precursors are known in the art. A preferred such precursor is Precursor 1 (below).

The second non-radioactive precursor is of Formula (III) as shown above. Such aminoxy functionalised peptides can be prepared by the methods of Poethko et al [J. Nucl. Med., 45, 892-902 (2004)], Schirrmacher et al [Bioconj. Chem., 18, 2085-2089 (2007)], Indrevoll et al [Bioorg.Med.Chem.Lett, 16, 6190-6193 (2006)], Glaser et al [Bioconj. Chem., 19, 951-957 (2008)] or Dall'Angelo et al [Org. Biomol. Chem., 11, 4551-4558 (2013)]. The aminoxy group may optionally be conjugated in two steps. First, the N-protected aminoxy carboxylic acid or N-protected aminoxy activated ester is conjugated to the peptide (e.g. via conjugation to the amine group of a Lys residue, or via conventional solid phase synthesis). Second, the intermediate N-protected aminoxy functionalised peptide is deprotected to give the desired product [see Solbakken and Glaser papers cited above]. N-protected aminoxy carboxylic acids such as Boc-aminoxyacetic acid [Boc-NH—O—CH$_2$(C=O)OH] and Eei-N—O—CH$_2$(C=O)OH are commercially available, e.g. from Sigma-Aldrich, Novabiochem and IRIS.

The term "protected" refers to the use of a protecting group. By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Amine protecting groups are well known to those skilled in the art and are suitably chosen from: Boc (where Boc is tert-butyloxycarbonyl); Eei (where Eei is ethoxyethylidene); Fmoc (where Fmoc is fluorenylmethoxycarbonyl); trifluoroacetyl; allyloxycarbonyl; Dde [i.e. 1-(4,4-dimethyl-2,6-dioxocyclohexylidene)ethyl] or Npys (i.e. 3-nitro-2-pyridine sulfenyl). The use of further protecting groups are described in *Protective Groups in Organic Synthesis,* 4$^{th}$ Edition, Theorodora W. Greene and Peter G. M. Wuts, [Wiley Blackwell, (2006)]. Preferred amine protecting groups are Boc and Eei, most preferably Eei.

In the method of the second aspect, the radiotracer solution of step (D) comprises said radiotracer in aqueous acetonitrile of 5 to 25% v/v acetonitrile content. The radiotracer solution of step (D) preferably comprises ethanol, and more preferably comprises both acetonitrile and ethanol. Ethanol has potentially multiple roles, since it can function as: a water-miscible organic solvent (as defined above); a radioprotectant or radiostabiliser; a 'biocompatible carrier' (as defined above; and as an antimicrobial preservative (as defined above). The present inventors have found that the combination of the 'radioprotectant' (as defined above) and ethanol is most effective to stabilise the radiotracers of the invention against radiolysis. The ethanol content of the radiotracer solution is preferably 0.5 to 5% v/v ethanol.

The purification step (E) removes species which remain bound to the SPE column—e.g. very lipophilic species or any particulates. Step (E) also removes hydrophilic impurities which exhibit low affinity for the SPE column stationary phase—and are thus removed in the loading and washing steps. Such hydrophilic impurities include any salts or ionic species (such as fluoride ion); catalysts (such as aniline); as well as the water-miscible organic solvent(s) from the radiotracer solution.

The radiotracer typically results from the conjugation of $^{18}$F-fluorobenzaldehyde (or similar) to an aminoxy-functionalised biological targeting moiety precursor, the conjugated fluorobenzaldehyde moiety confers additional lipophilicity to the conjugate. Hence, the radiotracer will tend to be retained on a reverse-phase SPE column, whereas the non-radioactive precursor itself (being more hydrophilic) will tend to be removed in the loading step and washing steps. Washing steps are also important to remove water-miscible organic solvent. In this way, the radiotracer solution is purified to remove unwanted non-radioactive impurities based on the biological targeting moiety which, if present, might compete with the radiotracer for biological sites of interest in vivo. Any more hydrophilic $^{18}$F-labelled, radioactive impurities will tend to be removed in a similar way. Thus, the initial level of Compound 2 in a preparation was 5 mg, which was reduced to ca. 200 µg (0.2 mg) in the purified radiotracer.

The SPE cartridge of the second aspect is preferably conditioned prior to use by treating first with a water-miscible organic solvent, then with a conditioning solution. Said water-miscible organic solvent is preferably ethanol, and said conditioning solution is suitably a 40-60% aqueous/water-miscible organic solvent mixture, more preferably 50% aqueous ethanol.

The radiotracer of step (C) and/or the radiotracer solution of step (D) are preferably cooled to a temperature range of 18 to 37° C., preferably 18 to 30° C.

The purification step (E) of the second aspect is preferably carried out as follows:
 (i) passing the radiotracer solution from step (D) through said reverse phase SPE cartridge, wherein the radiotracer is retained on said SPE cartridge;
 (ii) washing the SPE cartridge from step (i) one or more times with a wash solution which comprises an aqueous acetonitrile solution of said radioprotectant of 15 to 25% v/v acetonitrile content;
 (iii) washing the SPE cartridge from step (ii) one or more times with water or aqueous buffer solution;
 (iv) eluting the washed SPE cartridge of step (ii) or (iii) with an elution solvent which comprises said radioprotectant in an aqueous ethanol solution having an ethanol content of 35 to 80% v/v, wherein the eluent comprises purified radiotracer in said elution solvent.

The term "aqueous acetonitrile solution of said radioprotectant of 15 to 25% v/v acetonitrile content" refers to an aqueous solution (e.g. water itself, saline, an aqueous buffer or mixtures thereof), mixed with acetonitrile and possibly also ethanol (see below). Acetonitrile has the advantages that it is a good solvent for the radiotracer, is neither acidic nor basic, is relatively unreactive and thus compatible with a wide range of functional groups, and is highly miscible with water so that it is easily and completely removed (or at least down to ppm levels) by the washing of the SPE column in method steps (iii) and (iv). Acetonitrile was found to be the most efficient solvent for removal of impurities in the radiotracer, including aniline. The acetonitrile content of the radiotracer solution and wash solution preferably does not exceed 25% v/v, since higher levels risk loss of radiotracer product by elution from the SPE column. The acetonitrile content of the wash solution is preferably 18-22% v/v, more preferably 20-21% v/v.

The elution solvent of step (iv) preferably comprises 35-70% v/v aqueous ethanol, more preferably 40-60% v/v aqueous ethanol, most preferably 48-52% aqueous ethanol and especially preferably 50% aqueous ethanol.

The pH of the aqueous component of the radiotracer solution, wash solution, and elution solvent is preferably 7.5 to 8.5. That is preferably achieved using buffer solutions, more preferably phosphate buffer.

When the radioprotectant is sodium 4-aminobenzoate, a preferred concentration in the radiotracer solution is 5 mg/mL, and a preferred concentration in the wash solution and elution solvent is 2.5 mg/mL. An especially preferred radiotracer solution comprises 5 mg/mL sodium 4-aminobenzoate, 2% ethanol in a mixture of 79 g phosphate-buffered saline (pH 7.5) and 16.5 g acetonitrile. An especially preferred wash solution comprises 5 mg/mL sodium 4-aminobenzoate in phosphate-buffered saline (pH 7.5).

The SPE cartridge is preferably flushed between purification steps with air instead of nitrogen. Thus, the present inventors have found that the radioprotectant 4-aminobenzoic acid functions more effectively in the presence of air, as opposed to the situation where oxygen is excluded.

The purified radiotracer of step (iv) thus preferably contains 4-aminobenzoic acid, or a salt thereof with a biocompatible cation as radioprotectant, in 35-70% aqueous ethanol. For radiopharmaceutical applications, that is preferably diluted with an aqueous biocompatible carrier to give a final ethanol content of 0.1 to 10% v/v.

The method of the second aspect preferably further comprises:
 (H) dispensing the [$^{18}$F]-radiotracer radiopharmaceutical composition of step (G) into one or more syringes.

In a third aspect, the present invention provides a single use cassette as defined in the second aspect. Preferred embodiments of the cassette in the third aspect are as described in the second aspect (above).

In a fourth aspect, the present invention provides the use of an automated synthesizer apparatus as defined in the second aspect, to carry out the method of preparation of the second aspect. Preferred embodiments of the synthesizer and associated cassette in the fourth aspect are as described in the second aspect (above).

In a fifth aspect, the present invention provides the use of the cassette as defined in the second and third aspects, to carry out the method of preparation of the second aspect.

Preferred embodiments of the synthesizer and associated cassette in the fifth aspect are as described in the second aspect (above).

BRIEF DESCRIPTION OF THE DRAWINGS

FIG. 1 shows the radiation elution profile of Compound 3 through an SPE column, during the loading, washing and elution process using six radioactivity detectors positioned at various places on the FASTlab.

FIG. 2 shows a FastLab cassette configuration for the automated radiosynthesis and automated purification of Compound 3.

The invention is illustrated by the non-limiting Examples detailed below. Example 1 provides the synthesis of a c-Met targeting peptide of the invention ("Peptide 1"). Example 2 provides the synthesis of an aminoxy-functionalised Peptide 1 ("Compound 1"), wherein the aminoxy functional group is protected with a protecting group (Eei), and subsequent deprotection to give Compound 2. Example 3 provides the radiosynthesis of [$^{18}$F]-fluorobenzaldehyde. Example 4 is a comparative Example, which provides the radiosynthesis of the $^{18}$F-labelled conjugate Compound 3, without the methodology of the present invention. The RCP in this case is relatively low (79%) at the end of synthesis.

Example 5 provides an analysis of the identity and time-course of the radiochemical impurities in low RCP Compound 3 purified according to Example 4. This provides evidence that in-process radiolysis during attempted chromatographic purification was responsible for the low RCP. Example 5 provides information on the movement of radioactivity through the SPE column during SPE purification, demonstrating that the RAC is over 45 GBq/mL during the SPE process. This very high, but time-bound RAC, is also indicative of in-process radiolysis.

Example 7 provides an automated synthesis and purification of Compound 3, using an automated synthesizer and cassette. A significant increase in EOS yield was achieved by making up a MeCN/PBS purification solution containing 2.5 mg/Na-pABA, but the EOS RCP was still low, and vulnerable to high RAC (RCP=89% when a RAC of 660 MBq/mL, RCP=85% when a RAC of 844 MBq/ml in a 25 mL formulation). A high RAC at EOS indicates yet higher RAC on the cartridge during the later stages of the purification process. The RCP was improved further by increasing the Na-pABA content of the radiotracer solution to 5 mg/mL to 89-91%. Yet further improvements in RCP were obtained by adding HCl to the pABA wash solution to make it pH 4. The addition of ethanol (2%) to the radiotracer solution and wash solution resulted in a further improvement in RCP to >92%. The process of Example 7 removes 85% of peptide-related impurities and essentially all of the aniline (20 μg remaining out of 100,000 μg aniline present in the crude product before purification). The addition of the pABA and ethanol did not adversely affect the performance of the SPE purification with respect to the removal of chemical impurities.

Compounds of the Invention

| Name | Structure |
|---|---|
| Peptide 1 | Disulfide bridges at Cys4-16 and Cys6-14; Ac-Ala-Gly-Ser-Cys-Tyr-Cys-Ser-Gly-Pro-Pro-Arg-Phe-Glu-Cys-Trp-Cys-Tyr-Glu-Thr-Glu-Gly-Thr-Gly-Gly-Gly-Lys-NH$_2$ or Ac-AGSCYCSGPPRFECWCYETEGTGGGK-NH$_2$ |
| Compound 1 | [Peptide 1]–NH–C(O)–CH$_2$–O–N=C(CH$_3$)–O–Et |
| Compound 2 | [Peptide 1]–NH–C(O)–CH$_2$–O–NH$_2$ |
| Compound 3 | [Peptide 1]–NH–C(O)–CH$_2$–O–N=CH–C$_6$H$_4$–$^{18}$F |
| Precursor 1 | (CH$_3$)$_3$N$^+$–C$_6$H$_4$–CHO, CF$_3$SO$_2^-$ | where:
Compounds 1, 2 and 3 are functionalised at the epsilon amine group of the carboxy terminal Lys of Peptide 1; alternative stereochemistry at the oxime bond is possible, but not shown.

Abbreviations

Conventional single letter or 3-letter amino acid abbreviations are used.
Ac: Acetyl
Acm: Acetamidomethyl
ACN or MeCN: Acetonitrile.
AcOH: Acetic acid.
Boc: tert-Butyloxycarbonyl.
BTM: biological targeting moiety.
tBu: tertiary-butyl
DCM: Dichloromethane
DIPEA: N,N-Diisopropylethyl amine
DMF: Dimethylformamide
DMSO: Dimethylsulfoxide
Eei: ethoxyethylidine;
Eei-AOAc-OSu: N-(1-Ethoxyethylidene)-2-aminoxyacetic acid N-hydroxysuccinimidyl ester;
EOS: end of synthesis;
FBA: 4-fluorobenzaldehyde;
Fmoc: 9-Fluorenylmethoxycarbonyl;
HBTU: O-Benzotriazol-1-yl-N,N,N',N'-tetramethyluronium hexafluorophosphate;
HPLC: High performance liquid chromatography;
MW: molecular weight;
NHS: N-hydroxy-succinimide;
NMM: N-Methylmorpho line;
NMP: 1-Methyl-2-pyrrolidinone;
Pbf: 2,2,4,6,7-Pentamethyldihydrobenzofuran-5-sulfonyl;
RAC: radioactive concentration.
RCP: radiochemical purity.
RP-HPLC: reverse-phase high performance liquid chromatography;
tBu: tert-butyl;
TFA: Trifluoroacetic acid;
THF: Tetrahydrofuran;
TIS: Triisopropylsilane;
Trt: Trityl.

EXAMPLE 1

Synthesis of Peptide 1

Step (a): Synthesis of Protected Precursor Linear Peptide.
The precursor linear peptide has the structure:
Ac-Ala-Gly-Ser-Cys-Tyr-Cys(Acm)-Ser-Gly-Pro-Pro-Arg-Phe-Glu-Cys(Acm)-Trp-Cys-Tyr-Glu-Thr-Glu-Gly-Thr-Gly-Gly-Gly-Lys-NH$_2$
The peptidyl resin H-Ala-Gly-Ser(tBu)-Cys(Trt)-Tyr(tBu)-Cys(Acm)-Ser(tBu)-Gly-Pro-Pro-Arg(Pbf)-Phe-Glu(OtBu)-Cys(Acm)-Trp(Boc)-Cys(Trt)-Tyr(tBu)-Glu(OtBu)-Thr($\psi^{Me,Me}$pro)-Glu(OtBu)-Gly-Thr(tBu)-Gly-Gly-Gly-Lys(Boc)-Polymer was assembled on an Applied Biosystems 433A peptide synthesizer using Fmoc chemistry starting with 0.1 mmol Rink Amide Novagel resin. An excess of 1 mmol pre-activated amino acids (using HBTU) was applied in the coupling steps. Glu-Thr pseudoproline (Novabiochem 05-20-1122) was incorporated in the sequence. The resin was transferred to a nitrogen bubbler apparatus and treated with a solution of acetic anhydride (1 mmol) and NMM (1 mmol) dissolved in DCM (5 mL) for 60 min. The anhydride solution was removed by filtration and the resin washed with DCM and dried under a stream of nitrogen.

The simultaneous removal of the side-chain protecting groups and cleavage of the peptide from the resin was carried out in TFA (10 mL) containing 2.5% TIS, 2.5% 4-thiocresol and 2.5% water for 2 hours and 30 min. The resin was removed by filtration, TFA removed in vacuo and diethyl ether added to the residue. The formed precipitate was washed with diethyl ether and air-dried affording 264 mg of crude peptide.

Purification by preparative HPLC (gradient: 20-30% B over 40 min where A=H$_2$O/0.1% TFA and B=ACN/0.1% TFA, flow rate: 10 mL/min, column: Phenomenex Luna 5μ C18 (2) 250×21.20 mm, detection: UV 214 nm, product retention time: 30 min) of the crude peptide afforded 100 mg of pure Peptide 1 linear precursor. The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3μ C18 (2) 50×2 mm, detection: UV 214 nm, product retention time: 6.54 min). Further product characterisation was carried out using electrospray mass spectrometry (MH$_2^{2+}$ calculated: 1464.6, MH$_2^{2+}$ found: 1465.1).

Step (b): Formation of Monocyclic Cys4-16 Disulfide Bridge.
Cys4-16; Ac-Ala-Gly-Ser-Cys-Tyr-Cys(Acm)-Ser-Gly-Pro-Pro-Arg-Phe-Glu-Cys(Acm)-Trp-Cys-Tyr-Glu-Thr-Glu-Gly-Thr-Gly-Gly-Gly-Lys-NH$_2$.

The linear precursor from step (a) (100 mg) was dissolved in 5% DMSO/water (200 mL) and the solution adjusted to pH 6 using ammonia. The reaction mixture was stirred for 5 days. The solution was then adjusted to pH 2 using TFA and most of the solvent removed by evaporation in vacuo. The residue (40 mL) was injected in portions onto a preparative HPLC column for product purification.

Purification by preparative HPLC (gradient: 0% B for 10 min, then 0-40% B over 40 min where A=$H_2O$/0.1% TFA and B=ACN/0.1% TFA, flow rate: 10 mL/min, column: Phenomenex Luna 5µ C18 (2) 250×21.20 mm, detection: UV 214 nm, product retention time: 44 min) of the residue afforded 72 mg of pure Peptide 1 monocyclic precursor. The pure product (as a mixture of isomers P1 to P3) was analysed by analytical HPLC (gradient: 10-40% B over 10 min where A=$H_2O$/0.1% TFA and B=ACN/0.1% TFA, flow rate: 0.3 mL/min, column: Phenomenex Luna 3µ C18 (2) 50×2 mm, detection: UV 214 nm, product retention time: 5.37 min (P1); 5.61 min (P2); 6.05 min (P3)). Further product characterisation was carried out using electrospray mass spectrometry ($MH_2^{2+}$ calculated: 1463.6, $MH_2^{2+}$ found: 1464.1 (P1); 1464.4 (P2); 1464.3 (P3)).

Step (c): Formation of Second Cys6-14 Disulfide Bridge (Peptide 1).

The monocyclic precursor from step (b) (72 mg) was dissolved in 75% AcOH/water (72 mL) under a blanket of nitrogen. 1 M HCl (7.2 mL) and 0.05 M $I_2$ in AcOH (4.8 mL) were added in that order and the mixture stirred for 45 min. 1 M ascorbic acid (1 mL) was added giving a colourless mixture. Most of the solvents were evaporated in vacuo and the residue (18 mL) diluted with water/0.1 TFA (4 mL) and the product purified using preparative HPLC. Purification by preparative HPLC (gradient: 0% B for 10 min, then 20-30% B over 40 min where A=$H_2O$/0.1% TFA and B=ACN/0.1% TFA, flow rate: 10 mL/min, column: Phenomenex Luna 5µ C18 (2) 250×21.20 mm, detection: UV 214 nm, product retention time: 43-53 min) of the residue afforded 52 mg of pure Peptide 1. The pure product was analysed by analytical HPLC (gradient: 10-40% B over 10 min where A=$H_2O$/0.1% TFA and B=ACN/0.1% TFA, flow rate: 0.3 mL/min, column: Phenomenex Luna 3µ C18 (2) 50×2 mm, detection: UV 214 nm, product retention time: 6.54 min). Further product characterisation was carried out using electrospray mass spectrometry ($MH_2^{2+}$ calculated: 1391.5, $MH_2^{2+}$ found: 1392.5).

EXAMPLE 2

Synthesis, Purification and Lyophilization of Compound 2

Peptide 1 (0.797 g) and Eei-AOAc-OSu (IRIS Biotech; 127 mg) were dissolved in DMF (12 mL). DIPEA (100 µL) was added and the reaction mixture shaken for 26 min. A second aliquot of DIPEA (80 µL) was added and the reaction mixture shaken for 2 hr. The reaction mixture was then diluted with 10% ACN/water/0.1% ammonium acetate (40 mL), and the product purified by preparative HPLC using A=0.1% TFA/water and B=ACN with gradient elution of 20-40% B over 40 min. The fractions containing pure products (these are a mixture of Compound 1 and Compound 2) were pooled in a flask and the flask flushed with argon. The solution was stirred overnight to afford complete removal of Eei protecting groups. The deprotected product was lyophilised affording 550 mg (69% yield) of Compound 2.

The pure product was analysed by analytical LC-MS (gradient: 10-40% B over 5 min where A=$H_2O$/0.1% TFA and B=ACN TFA, flow rate: 0.6 mL/min, column: Phenomenex Luna 3µ C18 (2) 20×2 mm, detection: UV 214 nm, product retention time: 3.00 min), $MH_2^{2+}$ calculated: 1428.1, $MH_2^{2+}$ found: 1427.9).

EXAMPLE 3

Radiosynthesis of [$^{18}$F]-Fluorobenzaldehyde ($^{18}$F-FBA)

[$^{18}$F]-fluoride was produced using a GEMS PETtrace cyclotron with a silver target via the [$^{18}$O](p,n) [$^{18}$F] nuclear reaction. Total target volumes of 3.2-4.8 mL were used. The radio fluoride was trapped on a Waters QMA cartridge (pre-conditioned with carbonate), and the fluoride is eluted with a solution of Kryptofix$_{2.2.2}$. (5.14 mg) and potassium bicarbonate (1.40 mg) in water (800 µL) and acetonitrile (200 µL). Nitrogen was used to drive the solution off the QMA cartridge to the reaction vessel. The [$^{18}$F]-fluoride was dried for 9 minutes at 120° C. under a steady stream of nitrogen and vacuum. Trimethylammonium benzaldehyde triflate, [Precursor 1; Haka et al, J. Lab. Comp. Radiopharm., 27, 823-833 (1989)] (3.7 mg), in DMSO (2.0 mL) was added to the dried [$^{18}$F]-fluoride, and the mixture heated to 80° C. for 2 minutes to produce 4-[$^{18}$F]-fluorobenzaldehyde.

EXAMPLE 4

Radiosynthesis of Compound 3 (Comparative Example)

Compound 2 from Example 2 was radiolabelled with $^{18}$F using $^{18}$F-FBA from Example 3, then purified using a MCX+ SPE column, without the in-process radiostabilisation of the present invention, giving Compound 3 with an RCP of 79%.

EXAMPLE 5

Radiochemical Impurities in Low RCP Compound 3

The RCP of Compound 3 prepared as per Example 3 was studied as a function of time. The RCP did not drop further over time (up to 8 hours), showing that:
(i) Compound 3 is relatively radiostable at the RAC conditions existing at the end of the SPE process;
(ii) the RCP must already have been low at the end of the SPE process.

Analysis of Compound 3 from Example 4, i.e. without using the radiostabilisation methodology of the present invention and exhibiting low RCP (79%), found two radiolysis products to be the main contributors to the low RCP. These were identified by retention time on analytical HPLC, and comparison with the retention time of authentic samples of the non-radioactive analogues. These two radiolysis products are [$^{18}$F]4-fluorobenzaldehyde (FBA) and [$^{18}$F]4-fluorobenzonitrile (FPhCN), which together represented 12% of the radioactivity present in the low RCP Compound 3 preparation from Example 4.

These principal radiochemical impurities, which do not increase significantly with time, represent radiodegradation products of Compound 3, and in turn, in-process radiolysis.

EXAMPLE 6

SPE Elution Profile in the Purification of Compound 3

Six radioactivity detectors were positioned along a Fast-Lab cassette, with Detector #6 positioned towards the bottom of the SPE column of a preparation according to Example 7. The movement of radioactivity during the loading, washing, and elution steps of the SPE purification process was followed in this way.

The results are shown in FIG. 1. The crude product was shown to be trapped on the top of the SPE cartridge. As the purification proceeds, the radioactivity moved down the cartridge and towards the higher-numbered detectors, increasing their signal. This demonstrated that the radioactivity is not spread out over the entire cartridge, but concentrated in a tight band. During the purification, all the activity was concentrated into a volume of less than 1 mL, giving a RAC during purification (12-14 min) of 45,000 MBq/mL, i.e. 45 GBq/mL.

EXAMPLE 7

Automated Synthesis and Purification of Compound 3

A FastLab automated synthesizer (GE Healthcare Ltd) with cassette was used. The tC18 cartridge was obtained from Waters Limited (address as above). Precursor 1 was reacted with [$^{18}$F]-fluoride on the Fastlab according to Example 3 to give [$^{18}$F]-FBA. The [$^{18}$F]-FBA was reacted subsequently on the FastLab with Compound 2 (aminoxy derivative of Peptide 1), to give crude Compound 3.

Purification.

The cassette configuration is given in FIG. 2. Three external solvent vials are used on the cassette for the SPE purification:
Position 17=Anhydrous ethanol;
Position 18=Wash Solution of 5 mg/mL Na-pABA 2% EtOH in 79 g PBS/16.5 g MeCN, and HCl to bring to pH 4;
Position 20=Formulation Buffer of 34 mL PBS containing 80 mg Na-pABA.
Other Cassette Positions:
Position 21: Tubing to the tC18 cartridge in Position 22;
Position 22: tC18 cartridge (900 mg);
Position 23: Sterile filter.
FASTlab Procedure.

In the following, P17 etc refers to Position 17 of the cassette. S2 and S3 refer to syringe 2 and syringe 3:
(i) the first part of the purification process was conditioning with full S2 fill with ethanol from P17, followed by a full S2 fill of MeCN/PBS solution from P18.

(ii) crude Compound 3 in the aqueous ethanol solution from the conjugation step was diluted 1:1 with the formulation buffer from P20. This was done in two portions: half of the content of the crude volume from the reaction vessel was transferred to S2, and thereafter mixed with the same volume of formulation buffer from P20. This mixture was then slowly trapped onto the tC18 cartridge. After the first trapping, the same procedure was repeated with the remaining half of the crude.
(iii) S2 was rinsed with water and thereafter a full fill of S2 with the MeCN wash solution from P18. The MeCN wash solution was slowly pushed through the tC18 cartridge and to waste. This was repeated 5 more times—six such washes in total (but note that with Eei protecting group synthesis only a total of three washes are needed).
(iv) the MeCN on the tC18 cartridge was removed by solvent exchange: first 2× full fill of S2 with the formulation buffer from P20 followed by one full fill of S2 with water from the water bag.
(v) the eluent was made by mixing of 3 mL ethanol from P17 and 3 mL of formulation buffer from P20 in S2. The first 1 mL of the eluent was passed through the tC18 and to waste, the following 4 mL eluent was passed through the tC18 and the purified Compound 3 product collected in S3. After elution the product was transferred out from the FASTlab and into the product vial through P19.

The radiochemical purity (RCP) in this case was 92%.

The invention claimed is:

1. A method of preparation of the radiopharmaceutical composition comprising:
(A) reacting a first non-radioactive precursor with [$^{18}$F]-fluoride to give [$^{18}$F]-fluorobenzaldehyde in a single-use cassette comprising:
(i) a first non-radioactive precursor, that reacts with [$^{18}$F]-fluoride to give [$^{18}$F]-fluorobenzaldehyde, the first non-radioactive precursor having the formula I:

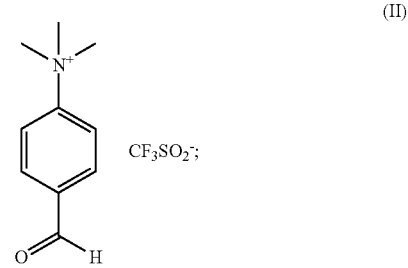

(II)

(ii) a second non-radioactive precursor of Formula III:

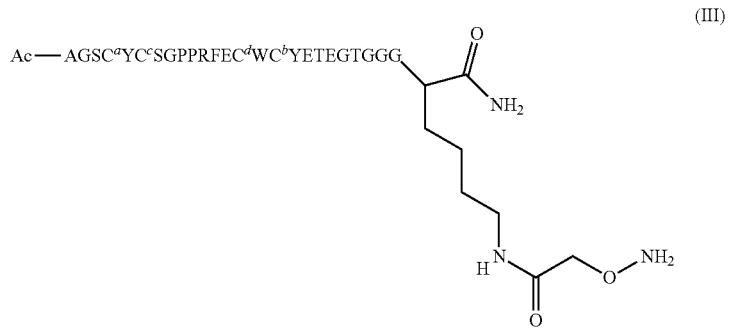

(III)

wherein $C^a$, $C^b$, $C^c$, and $C^d$ in Formula III are each cysteine residues and wherein $C^a$ and $C^b$ together and $C^c$ and $C^d$ together are cyclized to form two separate disulfide bonds;

(iii) a reverse phase solid phase extraction column;
(iv) a supply of the radioprotectant, wherein the radioprotectant is ascorbic acid, para-aminobenzoic acid, or gentisic acid;
(v) a reaction vessel;
(vi) at least one suitable solvent, wherein the at least one suitable solvent comprises aqueous acetonitrile of 5 to 25% v/v acetonitrile;

(B) reacting the [$^{18}$F]-fluorobenzaldehyde from step (A) with the second non-radioactive precursor to give a radiotracer of Formula II in a crude radiotracer solution:

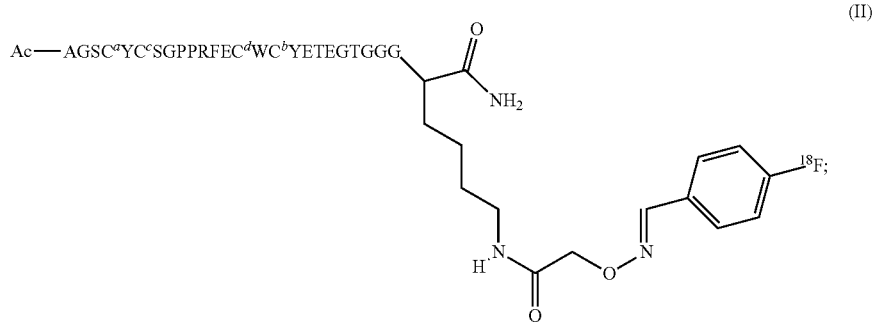

wherein $C^a$, $C^b$, $C^c$, $C^d$ in Formula II are each cysteine residues such that residues $C^a$ and $C^b$ as well as $C^c$ and $C^d$ are cyclized to form two separate disulfide bonds;
(C) adding said radioprotectant to the crude radiotracer solution from step (B) to form a second radiotracer solution, wherein the second radiotracer solution comprises said radiotracer of Formula II and said radioprotectant in aqueous acetonitrile of 5 to 25% v/v acetonitrile;
(D) purifying the second radiotracer solution from step (C) using said reverse phase solid phase extraction column to give a purified [$^{18}$F]-radiotracer solution;
(E) optionally diluting the purified [$^{18}$F]-radiotracer from step (D) with a biocompatible carrier;
(F) filtering the optionally diluted purified [$^{18}$F]-radiotracer solution from step (E) to give said radiopharmaceutical composition;
wherein said cassette fits removably and interchangeably onto an automated synthesizer apparatus and at least steps (A)-(D) are carried out in the automated synthesizer apparatus.

2. The method of claim 1, where the steps (A)-(F) are carried out in the automated synthesizer apparatus.

3. The method of claim 1, where the second radiotracer solution of step (C) further comprises 0.5 to 5% v/v ethanol.

4. The method of claim 1, where the purification step (D) is carried out as follows:
(i) passing the purified [$^{18}$F]-radiotracer solution from step (D) through said reverse phase SPE cartridge, wherein the [$^{18}$F]-radiotracer of Formula II is retained on said SPE cartridge;
(ii) washing the SPE cartridge from step (i) one or more times with a wash solution which comprises an aqueous acetonitrile solution of said radioprotectant of 15 to 25% v/v acetonitrile content;
(iii) washing the SPE cartridge from step (ii) one or more times with water or aqueous buffer solution;
(iv) eluting the washed SPE cartridge of step (ii) or (iii) with an elution solvent which comprises said radioprotectant in an aqueous ethanol solution having an ethanol content of 35 to 80% v/v,
wherein the eluent comprises purified radiotracer in said elution solvent.

5. The method of claim 1, wherein the SPE cartridge is a $C^{18}$ SPE cartridge.

6. The method of claim 5, where the elution solvent of step (iv) comprises 40-60% v/v aqueous ethanol.

7. The method of claim 5, which further comprises:
(G) dispensing the [$^{18}$F]-radiotracer radiopharmaceutical composition of step (F) into one or more syringes.

8. A single use cassette comprising:
a first non-radioactive precursor, that reacts with [$^{18}$F]-fluoride to give [$^{18}$F]-fluorobenzaldehyde, the first non-radioactive precursor having the formula I:

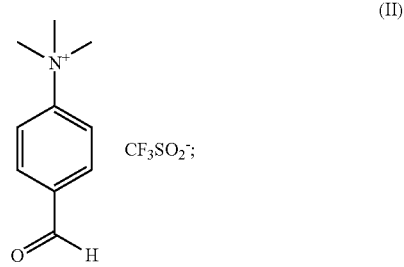

a second non-radioactive precursor of Formula III:

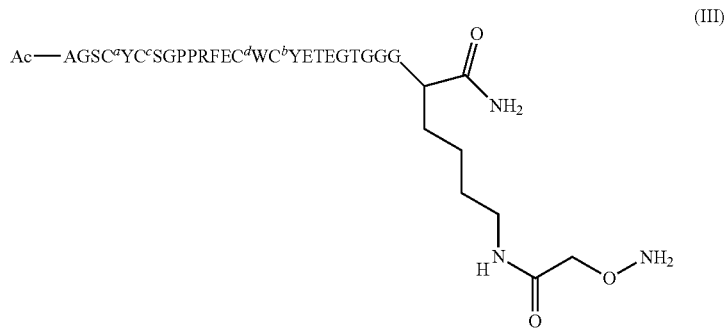

(III)

wherein $C^a$, $C^b$, $C^c$, and $C^d$ in Formula III are each cyssteine residues and wherein $C^a$ and $C^b$ together and $C^c$ and $C^d$ together are cyclized to form two separate disulfide bonds;
a reverse phase solid phase extraction column;
a supply of radioprotectant, wherein the radioprotectant is ascorbic acid, para-aminobenzoic acid, or gentisic acid;
a reaction vessel; and
at least one suitable solvent, wherein the at least one suitable solvent comprises aqueous acetonitrile of 5 to 25% v/v acetonitrile.

* * * * *